United States Patent [19]

Bain

[11] 4,367,769
[45] Jan. 11, 1983

[54] SAFETY CONNECTOR FOR FLEXIBLE TUBE DEVICE

[76] Inventor: James Bain, 1650 Gloucester Rd., London, Ontario, Canada, N6S 2S6

[21] Appl. No.: 925,393

[22] Filed: Jul. 17, 1978

[51] Int. Cl.³ .............................................. F16L 11/12
[52] U.S. Cl. ...................................... 138/114; 285/12; 285/155; 285/177; 285/222; 138/103; 138/178; 285/423; 604/23; 604/100
[58] Field of Search ................ 138/114, 103, 177, 178; 4/DIG. 7; 285/133 R, 155, 156, 158, 177, 258, 382.4, 12, 222, 423; 137/561 A; 128/349 R

[56] References Cited

U.S. PATENT DOCUMENTS

| 725,275 | 4/1903 | McLean | 285/155 X |
|---|---|---|---|
| 3,466,738 | 9/1969 | Mount | 285/382.4 X |
| 3,486,730 | 12/1969 | Potash | 285/177 X |
| 3,707,972 | 1/1973 | Villari et al. | 285/12 X |
| 3,768,476 | 10/1973 | Raitto | 285/423 X |
| 3,856,051 | 12/1974 | Bain | 138/114 |
| 4,013,310 | 3/1977 | Dye | 285/423 X |
| 4,031,916 | 6/1977 | Camerano | 285/222 X |

FOREIGN PATENT DOCUMENTS

| 1220252 | 4/1902 | France | 285/177 |
|---|---|---|---|
| 1184350 | 7/1959 | France | 285/155 |
| 1192836 | 10/1959 | France | 285/155 |
| 103618 | 1/1964 | Norway | 285/155 |

Primary Examiner—James E. Bryant, III
Attorney, Agent, or Firm—Eric P. Schellin

[57] ABSTRACT

A flexible tubular assembly having an outer tube and located therein an inner tube. One end of the inner tube is in communication with the locale of the nasal passages of a patient. The other end of the inner tube is provided with the safety connector at an end portion of the outer tube externally with respect to the outside of the connector through a wall thereof. The external connection includes a tubular nipple that is at an angle with respect to the connector and is the safety connector feature of the present invention.

2 Claims, 2 Drawing Figures

U.S. Patent    Jan. 11, 1983    4,367,769
FIG. 1.
FIG. 2.
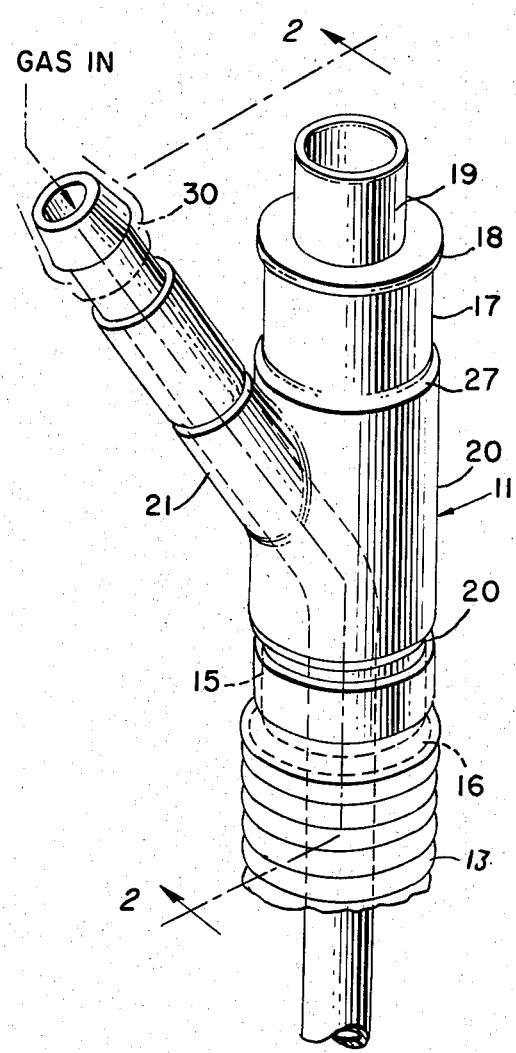
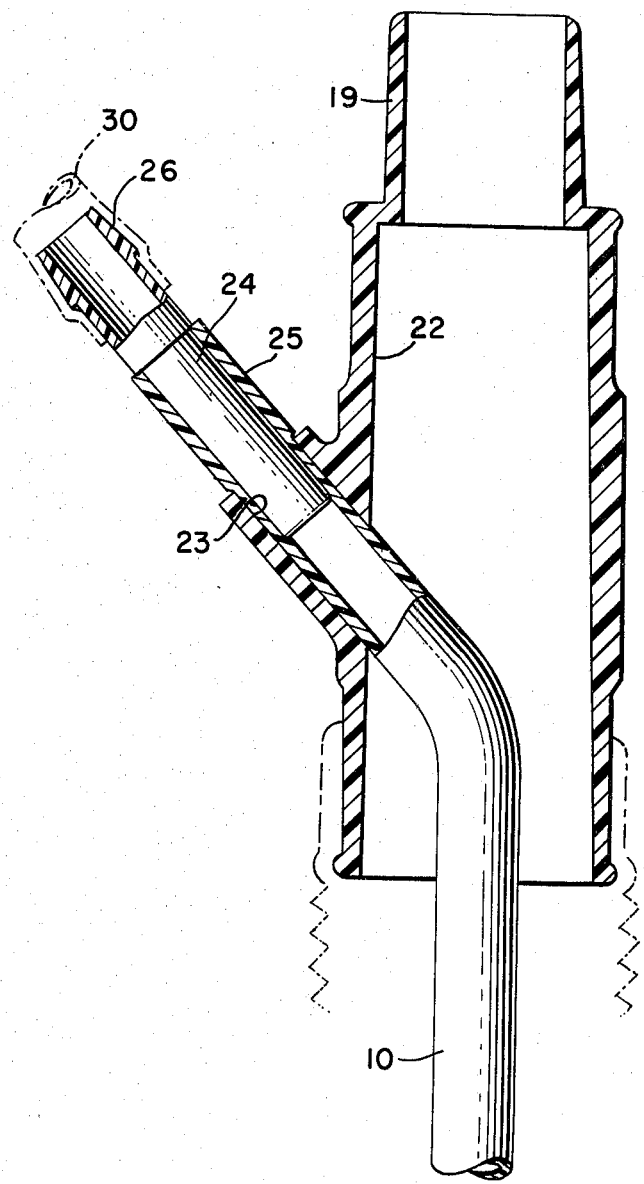

SAFETY CONNECTOR FOR FLEXIBLE TUBE DEVICE

BACKGROUND OF THE INVENTION

This invention relates to an anaesthetic device which is a safety connector an is an improvement over the invention disclosed and claimed in the most relevant prior art patent, namely, the patent to Bain, U.S. Pat. No. 3,856,051.

In partial rebreathing anaesthetic systems various types of systems and devices have been disclosed. However, it has been said that such systems suffer from convenience of operation and simplicity when they are employed.

The aforementioned patentee Bain disclosed a system and a device which eliminates the use of a plurality of separate tubes for such circuit and provides means for supplying an anaesthetic gas closely to the nasal and oral passages of a patient. It also produces a simpler more convenient means of directing anaesthetic gas to a patient.

In the said system a first flexible corrugated thin walled tubular member is employed for exhalation from the patient. Located internally of the first tubular member is a second flexible tubular member of considerably smaller diameter. The second tubular member is designed to carry the anaesthetic gas. One end of each of the tubes terminate at the locale of the patient. The other ends terminate in a tubular rigid connector. The first flexible tubular member terminates externally of one end of said tubular connector. The rigid tubular connector has a tubular elbow which extends through a wall of the rigid tubular connector. The elbow is adapted and constructed to accept the end of the second tubular member internally of said rigid tubular connector.

It is the fact of this connection that has proved to be a considerable problem. The device disclosed in the aforementioned patent is designed to be disposable. However, it has been found that the device is in fact employed on repeated occasions. Unfortunately, with a number of uses, including autoclaving, the second flexible tube connected to the elbow has on occasion become disengaged whereby the anaesthetic gas spills into the confines of the first flexible tubular member to the detriment of the patient. Due to the fact that the connection to the elbow with the second flexible tubular member is internally with respect to the rigid tubular connector, one cannot visually inspect the device to determine whether the aforementioned internal connection is still in engagement.

By means of the present invention the connections of the rigid tubular connector have been ingeniously rearranged to avoid the above mentioned problem.

BRIEF DESCRIPTION OF THE INVENTION

The present invention is an improvement of a rigid tubular connector shown in the patent to Bain, U.S. Pat. No. 3,856,051. Instead of providing a tubular elbow having one end terminating axially in said rigid tubular connector and the other end passing through a wall of the connector and normal thereto, the connector is provided with a stub having a bore therethrough. In this fashion the flexible tube instead of terminating by attachment to the end portion of the elbow in the connector, where it cannot be seen, the flexible tube is carried externally of said connector through said stub. Suitable connections to an anaesthetic gas carrying line is then made to the flexible tube.

BRIEF DESCRIPTION OF THE DRAWINGS

FIG. 1 is a perspective view of the device of the present invention. FIG. 2 is a cross-sectional view of the device taken along line 2—2 of FIG. 1.

DETAILED DESCRIPTION OF THE INVENTION

Referring to FIG. 1 there is shown a connector 11 for a corrugated flexible conduit 12 including a first corrugated tubular member 13 preferably composed of corrugated flexible plastic for friction enegaging with the connector by being placed coaxially thereon in order to communicate with a patient mask at the other end (not shown). As in the prior art of U.S. Pat. No. 3,856,051, a second flexible tubular member 10 is, for a substantial portion of its length, interiorly disposed and preferably attached to the interior walls of the first flexible tubular member 13 by appropriate means, as by solvent bonding or adhesive.

The connector 11 has an elongated cylindrical configuration. It possesses a first male connection means 15 having a widened portion 16 for the flexible corrugated tubular member that is connected thereto by a friction fit as noted. The other end is also provided with a second male connection means 17 having a widened portion 18 adapted and constructed to receive the tubular connection, which may ultimately communicate with a breathing bag (not shown). On the other hand the connector at the noted other end possesses a smaller outer annular surface 19, slightly tapered, which is adapted to mate with a conventional breathing tube or suitable valving arrangement (not shown).

The connector has a wider annular portion 20 than either of the male connector means 15 and 17. It should be noted that thereby male connector means 15 is provided with a stop shoulder 20 and male connector means 17 is provided with a stop shoulder 27. These stops will effectively control the extent to which a conduit may be mounted. Even though the annular portion is of larger diameter it will be noted that the inner bore 22 therein is uniform, except for the smaller outer annular surface 19.

The annular portion 20 has outwardly extending therefrom a tube 21 which is at an angle with respect to the axis of the connector, preferably about 45°, as shown. It will be noted that the bore 23 through 21 is of a dimension to accommodate the end portion of second flexible tubular member 10 in a fairly snug manner. The end of the tubular member 10 is provided with a relatively short tubular stub 24 which has a diameter to distend slightly the end portion 25 of tubular member 10 in that portion thereof into which it is positioned. A relatively small end portion of stub 24 extends into bore 23 to provide a rigid connection. The distension of the end portion 25 will prevent the withdrawal of the flexible tubular member 10 into the connector 11.

The other end of the tubular stub 24, not positioned in the flexible tubular member 10, terminates in a nipple 26 which consists of a wider annular portion tapering downwardly axially away from the end affixed to flexible tubular member 10. The figures depict in dotted lines a fragmentary portion of a flexible tube 30 which tube is adapted and constructed to carry an anesthetic gas for transmittal to tubular member 10 and eventually to the patient.

In view of the ingenious set up of the present invention all attaching parts of the gas connection are external of the connector 11 so that such parts are visible in the event there is a discontinuity. For instance in the event flexible tube 30 becomes disconnected from the nipple 26, it will be visible. Additionally, in the event tubular stub 24 becomes disengaged from the end of flexible tubular member 10, such will also be noted especially if the member 10 is somehow withdrawn into the connector 11. It will therefore be acknowledged that the present connector constitutes considerable improvement over the prior art device and arrangement as mentioned and exemplified in U.S. Pat. No. 3,856,051.

What is claimed is:

1. A connector comprising a rigid tubular member, said rigid tubular member having in axial alignment a first tubular end portion and a second tubular end portion, said tubular member having a substantially centrally located portion, a first flexible tubing having an end portion concentrically frictionally positioned on said first end portion, said second end portion having a tube stub extending axially beyond said second end portion and of a diameter less than said second end portion, said centrally located portion having a tubular stub having a bore therethrough in communication internally with respect to said rigid tubular member and at an angle less than 90° with respect to the axis of said rigid tubular member in the direction towards said second end portion, said tubular stub having a second flexible tubing threaded therethrough into said rigid tubular member and through said first flexible tubing, said second flexible tubing having an end portion extending beyond said tubular stub, said end portion of said second flexible tubing being fitted with a tubular connecting means, said tubular connecting means having a portion fitted internally of said second flexible tubing and having a diameter to distend the said end portion and a portion of the tubular connecting means extends into said tubular stub.

2. The connector of claim 1 wherein the first flexible tubing is corrugated.

* * * * *